(12) United States Patent
Saito et al.

(10) Patent No.: US 12,173,028 B2
(45) Date of Patent: Dec. 24, 2024

(54) METHOD FOR PRODUCING GLYCOSIDE COMPOUND

(71) Applicant: SUMITOMO CHEMICAL COMPANY, LIMITED, Chuo-ku (JP)

(72) Inventors: Tatsuya Saito, Osaka (JP); Hideki Ihara, Osaka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 798 days.

(21) Appl. No.: 17/273,988

(22) PCT Filed: Sep. 6, 2019

(86) PCT No.: PCT/JP2019/035241
§ 371 (c)(1),
(2) Date: Mar. 5, 2021

(87) PCT Pub. No.: WO2020/050411
PCT Pub. Date: Mar. 12, 2020

(65) Prior Publication Data
US 2021/0355153 A1 Nov. 18, 2021

(30) Foreign Application Priority Data
Sep. 7, 2018 (JP) .................................. 2018-168135

(51) Int. Cl.
*C07H 23/00* (2006.01)
*C07H 19/06* (2006.01)
*C07H 19/10* (2006.01)

(52) U.S. Cl.
CPC ............. *C07H 23/00* (2013.01); *C07H 19/06* (2013.01); *C07H 19/10* (2013.01)

(58) Field of Classification Search
None
See application file for complete search history.

(56) References Cited

U.S. PATENT DOCUMENTS

| | | |
|---|---|---|
| 5,371,202 A | 12/1994 | Hasegawa |
| 2007/0282097 A1 | 12/2007 | Ohgi et al. |

(Continued)

FOREIGN PATENT DOCUMENTS

| | | |
|---|---|---|
| CN | 101048423 A | 10/2007 |
| CN | 101421289 A | 4/2009 |

(Continued)

OTHER PUBLICATIONS

Shiba et al., Chemical synthesis of a very long oligoribonucleotide with 2-cyanoethoxymethyl (CEM) as the 2′-O-protecting group: structural identification and biological activity of a synthetic 110mer precursor-microRNA candidate, Nucleic Acids Research, vol. 35, Issue 10, May 15, 2007, pp. 3287-3296.*

(Continued)

*Primary Examiner* — Patrick T Lewis
(74) *Attorney, Agent, or Firm* — Oblon, McClelland, Maier & Neustadt, L.L.P.

(57) ABSTRACT

A process for preparing a glycoside compound represented by formula (3), which includes reacting a glycoside compound represented by formula (1) with an ether compound represented by formula (2) in the presence of an oxidizing agent and an acid to prepare a glycoside compound represented by formula (3),

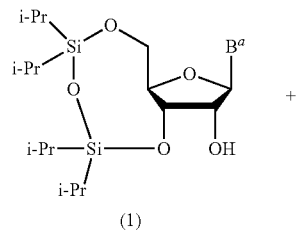

(1)

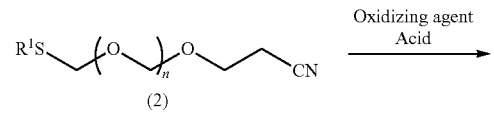

(2)

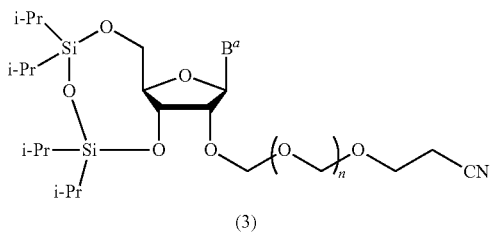

(3)

where the oxidizing agent is added to a reaction system, followed by adding an acid thereto,
where $B^a$ represents a cytosine group which may be optionally substituted with acyl group, or an uracil group, $R^1$ represents a C1 to C6 alkyl group or a phenyl group, and n is 0 or 1, where an oxidizing agent is selected from N-halogenated succinimide and N-halogenated hydantoin, and an acid is selected from perfluoroalkylcarboxylic acid, alkylsulfonic acid, arylsulfonic acid, periluoroalkylsulfonic acid, and salts thereof, and any combinations thereof, which can provide a synthesis of a desired compound with high purity.

16 Claims, No Drawings

(56) References Cited

U.S. PATENT DOCUMENTS

| | | | |
|---|---|---|---|
| 2009/0312534 A1 | 12/2009 | Kitagawa et al. | |
| 2014/0206856 A1 | 7/2014 | Aoki et al. | |
| 2018/0079768 A1 | 3/2018 | Aoki et al. | |

FOREIGN PATENT DOCUMENTS

| | | | |
|---|---|---|---|
| CN | 101426804 A | 5/2009 | |
| CN | 101426805 A | 5/2009 | |
| CN | 101522701 A | 9/2009 | |
| CN | 103906758 A | 7/2014 | |
| CN | 107428793 A | 12/2017 | |
| CN | 110198948 A | 9/2019 | |
| CN | 112020507 A | 12/2020 | |
| JP | 5-78381 A | 3/1993 | |
| JP | WO2010/079813 A1 | 6/2012 | |
| JP | 5157168 B2 | 3/2013 | |
| JP | 5554881 B2 | 7/2014 | |
| KR | 10-2017-0129264 A | 11/2017 | |
| WO | WO 2007/097447 A1 | 8/2007 | |
| WO | WO 2011/125943 A1 | 10/2011 | |
| WO | WO 2013/027843 A1 | 2/2013 | |
| WO | WO 2016/159374 A1 | 10/2016 | |

OTHER PUBLICATIONS

Extended European Search Report issued on Apr. 13, 2022 in European Patent Application No. 19856557.4, 10 pages.

Ohgi et al., "A New RNA Synthetic Method with a 2'-O-(2-Cyanoethoxymethyl) Protecting Group", Organic Letters, vol. 7, No. 16, 2005, pp. 3477-3480, XP003009345.

Office Action issued Sep. 5, 2023, in corresponding Japanese Patent Application No. 2020-541322 (with English Translation), 8 pages.

Indian Office Action issued Aug. 30, 2022 in Indian Patent Application No. 202117015774, 7 pages.

Office Action issued Apr. 4, 2023, in corresponding Japanese Patent Application No. 2020-541322 (with English Translation), 8 pages.

International Search Report issued Nov. 26, 2019 in PCT/JP2019/035241 (submitting English translation only), 2 pages.

Written Opinion of the International Searching Authority issued Nov. 26, 2019 in PCT/JP2019/035241 (submitting English translation only), 7 pages.

C. H. M. Verdegaal, et al., "Acid-Catalyzed Isomerization of the Tetraisopropyldisiloxane-1, 3-diyl Group. Simultaneous Protection of Two Secondary Alcoholic Functions" Tetrahedron Letters, vol. 21, No. 16, 1980, pp. 1571-1574.

Scott G. Petersen et al., "o-Nitrobenzenesulfonamides in Nucleoside Synthesis: Efficient 5'-Aziridination of Adenosine" The Journal of Organic Chemistry, vol. 70, No. 15, 2005, pp. 5833-5839.

Combined Chinese Office Action and Search Report issued Mar. 18, 2024, in corresponding Chinese Patent Application No. 201980058307.8 (with English Translation) 36 pages.

J. Kremser et al., "Chemical synthesis and NMR spectroscopy of long stable isotope labelled RNA", Chemical Communications, vol. 53, Issue 96, 2017, pp. 12938-12941.

* cited by examiner

METHOD FOR PRODUCING GLYCOSIDE COMPOUND

TECHNICAL FIELD

This application claims priority to and the benefit of Japanese Patent Application No. 2018-168135 filed Sep. 7, 2018, the entire contents of which are incorporated herein by reference.

The present invention relates to a glycoside compound and a process for preparing an amidite compound.

BACKGROUND ART

RNA can be applied as a RNA probe, an antisense RNA, a siRNA, or an aptamer and so on, which is a useful material.

RNA can be synthesized by a solid phase synthesis, and in the solid phase synthesis, a phosphoramidite of nucleoside (hereinafter, referred to as "amidite") is used as a raw material. As examples of the protecting group of a hydroxy group at 2' position of the amidite, TBDMS (t-butyl dimethyl silyl), TOM (triisopropylsilyloxy methyl), ACE (bis (2-acetoxyethoxy)methyl) and the others have been known. Further, though the protecting groups disclosed in Patent Literatures 1, 2 and 3 have been reported as the protecting group of a hydroxy group at 2' position of amidite, a synthesis method for the amidite containing these protecting groups isn't necessary sufficient in terms of yield or purity of the obtainable amidite.

It have been known that when any position isomer of an amidite is present, the position isomer may affect adversely a synthesis of a final product in a synthesis of RNA (see: He, Kaizhang and Hasan, Ahmad Classification and Characterization of Impurities in Phosphoramidites Used in Making Therapeutic Oligonucleotides: Risk Mitigation Strategies for Entering Clinical Phases, <URL: https://assets.thermofisher.com/TFS-Assets/BID/Technical-Notes/amidite-impurity-classification-technote.pdf>).

CITATION LIST

Patent Literature

Patent Literature 1: JP 5157168 B2
Patent Literature 2: JP 5554881 B2
Patent Literature 3: WO 2007/097447

SUMMARY OF THE INVENTION

Problems to be Solved by Invention

An object of the present invention is to provide a glycoside compound or an amidite compound, which can provide a synthesis of a desired compound (an amidite compound) with high purity.

Means to Solve Problems

For the synthesis of amidite, according to the above-mentioned Patent Literatures 1, 2 and 3, the preparation of the glycoside compound represented by the following general formula (3) is conducted by adding an acid such as trifluoromethanesulfonic acid or silver trifluoromethanesulfonate to a reaction system, followed by adding any oxidizing agent such as N-iodosuccinimide and N-bromosuccinimide thereto. As a result, it has been confirmed by a mass analysis that any impurity materials having the same molecular weight as those of a desired compound are formed.

The present inventors have intensively studied to achieve the above object, and as a result, obtained the findings that during a preparation of the glycoside compound represented by general formula (3) in a synthesis of an amidite compound, a formation of impurity materials having the same molecular weight as those of the desired compound can be suppressed by adding an oxidizing agent (N-iodosuccinimide) to a reaction system, followed by adding an acid (trifluoromethanesulfonic acid) thereto. As a result, the synthesis of the desired compound (amidite compound) with high purity can be achieved.

The present invention have been completed by repeating further considerations on the basis of these findings, and accordingly provide the process for preparing glycoside compound and amidite compound. The present invention encompasses aspects described in the below-mentioned Items, but are not limited thereto.

Item 1. A process for preparing a glycoside compound represented by general formula (3), which comprises the following step:

Step A: a step of reacting a glycoside compound represented by general formula (1) with an ether compound represented by formula (2) in the presence of an oxidizing agent and an acid to prepare a glycoside compound represented by general formula (3), wherein the oxidizing agent is added to the reaction system, followed by adding an acid thereto.

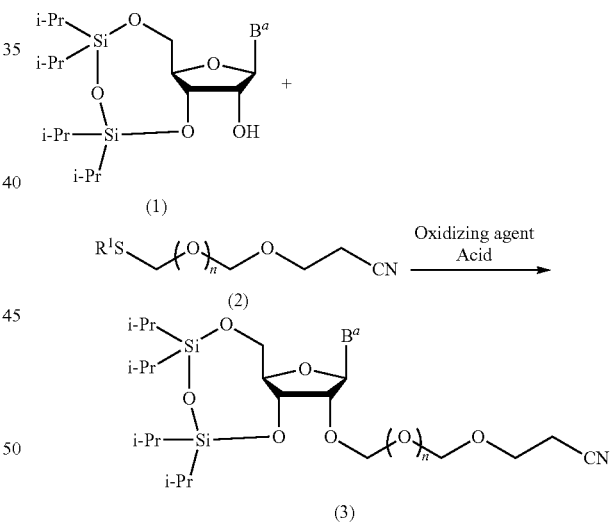

(wherein
$B^a$ represents a cytosine group which may be optionally substituted with acyl group, or an uracil group,
$R^1$ represents a C1 to C6 alkyl group or a phenyl group, and
n is 0 or 1),
wherein
the oxidizing agent is selected from the group consisting of N-halogenated succinimide and N-halogenated hydantoin, and
the acid is selected from the group consisting of perfluoroalkylcarboxylic acid and salts thereof, alkylsulfonic acid and salts thereof, aryl sulfonic acid and salts thereof, perfluoroalkylsulfonic acid and salts thereof, and any combinations of two kinds or more thereof.

Item 2. The process described in Item 1 wherein n is 1.

Item 3. The process described in Item 1 wherein n is 0.

Item 4. The process described in any one of Items 1 to 3 wherein the oxidizing agent is N-halogenated succinimide.

Item 5. The process described in any one of Items 1 to 4 wherein the oxidizing agent is N-iodosuccinimide.

Item 6. The process described in any one of Items 1 to 5 wherein the acid is at least one acid selected from the group consisting of trifluoromethanesulfonic acid, silver trifluoromethanesulfonate, and methanesulfonic acid.

Item 7. The process described in any one of Items 1 to 6 wherein the acid is trifluoromethanesulfonic acid.

Item 8. The process described in any one of Items 1 to 7 wherein tetrahydrofuran is used as a solvent.

Item 9. The process described in any one of Items 1 to 8 wherein $R^1$ represents a methyl group.

Item 10. The process described in any one of Items 1 to 9 wherein $B^a$ represents a cytosine group substituted with acetyl group, or an unsubstituted uracil group.

Item 11. A process for preparing an amidite compound represented by general formula (I):

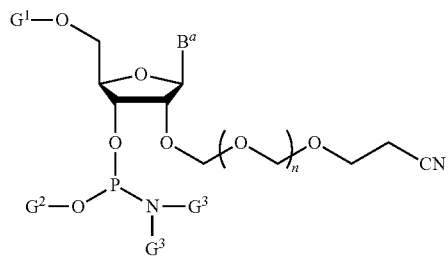

(I)

(wherein
$B^a$ and n are the same as defined above,
$G^1$ and $G^2$ are identical to or different from each other, and represent a protecting group for a hydroxy group, and
$G^3$ are identical to or different from each other, and represent an alkyl group), Step A: a step of reacting a glycoside compound represented by general formula (1) with an ether compound represented by formula (2) according to any one of the process described in any one of Items 1 to 10 to prepare a glycoside compound represented by general formula (3).

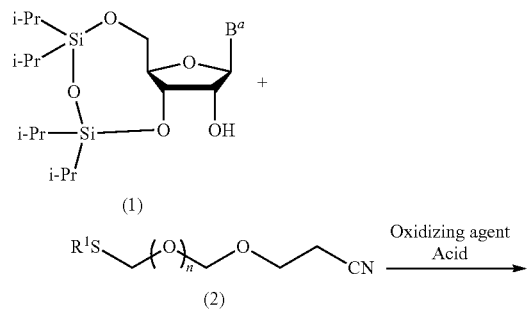

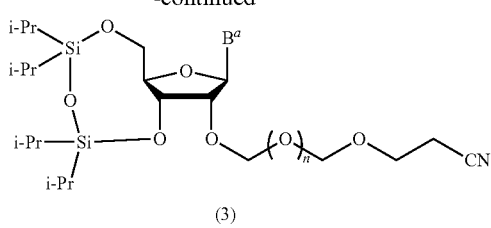

(3)

(wherein $B^a$, $R^1$ and n are the same as defined above.)

Item 12. The process described in Item 11, which further comprises the following step:

step (B): a step of deprotecting hydroxy groups at 3' position and 5' position of the glycoside compound represented by general formula (3) to prepare a glycoside compound represented by general formula (4).

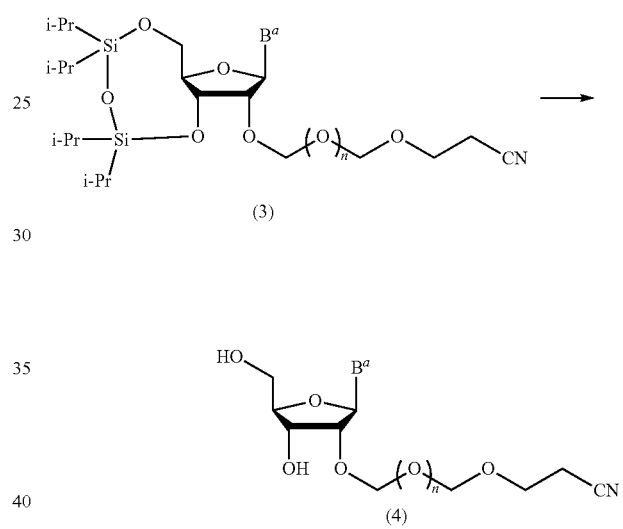

(wherein $B^a$ and n are the same as defined above.)

Item 13. The process described in Item 12, wherein triethylamine trihydrofluoride or pyridine hydrofluorate is used as a deprotecting agent.

Item 14. The process described in Item 12 or 13, which further comprises the following step:

Step C: a step of introducing a protecting group $G^1$ to a hydroxy group at 5' position of the glycoside compound represented by general formula (4) which is obtained in the step (B), followed by subjecting a hydroxy group at 3' position to a phosphoramidation reaction to prepare an amidite compound represented by general formula (I).

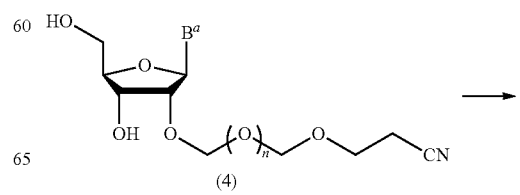

-continued

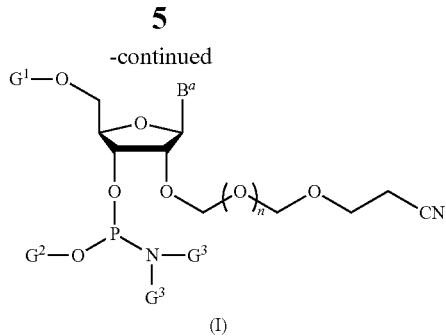

(I)

(wherein $B^a$, n, $G^1$, $G^2$ and $G^3$ are the same as defined above).

Item 15. The process described in Item 14 wherein 4,4'-dimethoxy tritylchloride is used as a reagent for introducing a protecting group for hydroxy group at 5' position.

Item 16. The process described in Item 14 or 15 wherein 2-cyanoethyl-N,N,N',N'-tetraisopropylphosphorodiamidite as a reagent for phosphoramidation of a hydroxy group at 3' position.

Effect of Invention

According to the process of the present invention, in the reaction for synthesizing an amidite compound, a formation of impurities of intermediate compounds can be suppressed, and as a result, the desired compound (amidite compound) can be prepared with a high purity.

Hereinafter, the present invention is explained in detail.

As used herein, the term "comprise" may encompass the meanings of "essentially consist of" and "consist of".

MODE FOR CARRYING OUT THE INVENTION

The present invention relates to a process for preparing an amidite compound represented by general formula (I), which is characterized by comprising the following step A, steps A and B, or steps A to C.

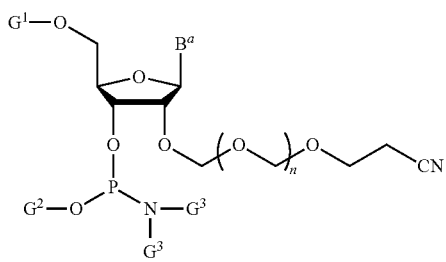

(I)

(wherein $B^a$ represents a cytosine compound which may be optionally substituted with acyl group, or an uracil group, n is 0 or 1, $G^1$ and $G^2$ are identical to or different from each other, and represent a protecting group for hydroxy group, and $G^3$ are identical to different from each other, and represents an alkyl group).

Step A: a step of reacting a glycoside compound represented by general formula (1) with an ether compound represented by formula (2) in the presence of an oxidizing agent and an acid to prepare a glycoside compound represented by general formula (3), wherein an oxidizing agent is added to a reaction system, followed by adding an acid thereto,

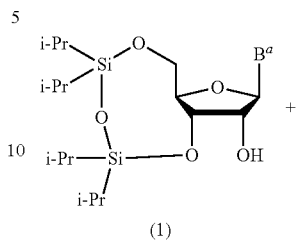

(1)

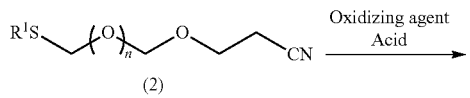

(2)

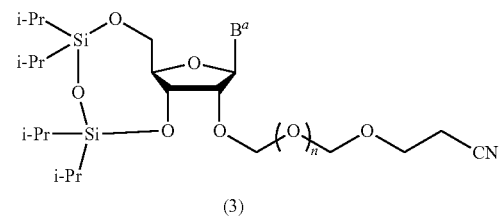

(3)

(wherein $B^a$ and n are the same as defined above, and $R^1$ represents a C1 to C6 alkyl group, or a phenyl group)

Step (B): a step of deprotecting hydroxy groups at 3' position and 5' position of the glycoside compound represented by general formula (3) which is obtained in the step A to prepare a glycoside compound represented by general formula (4).

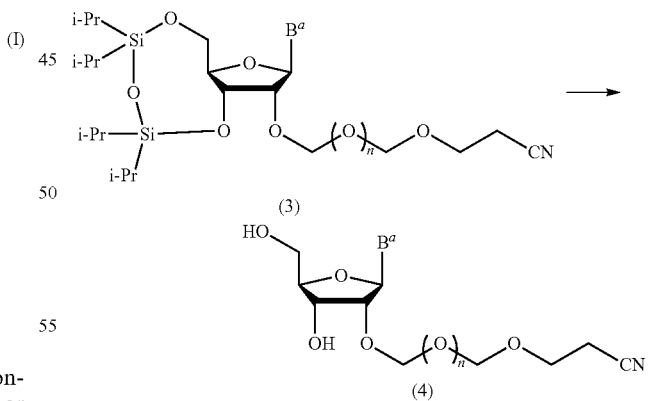

(wherein $B^a$ and n are the same as defined above.)

Step C: a step of introducing a protecting group $G^1$ into a hydroxy group at 5' position of the glycoside compound represented by general formula (4) which is obtained in the step (B), followed by subjecting a hydroxy group at 3' position to a phosphoramidation reaction to prepare an amidite compound represented by general formula (I).

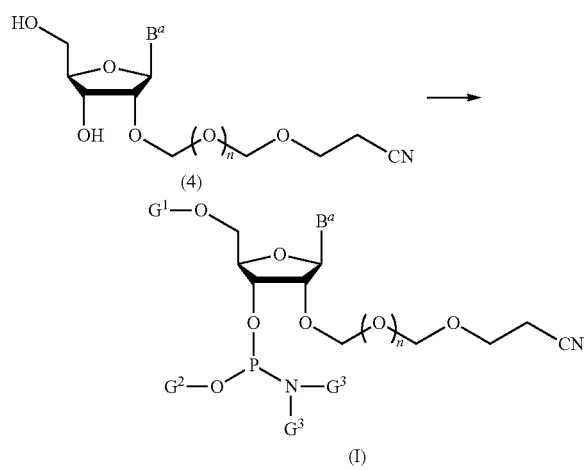

(wherein $B^a$, n, $G^1$, $G^2$ and $G^3$ are the same as defined above)

Examples of $R^1$ includes preferably a methyl group.

Examples of nucleic acid base as $B^a$ include the following cytosine group, or uracil group.

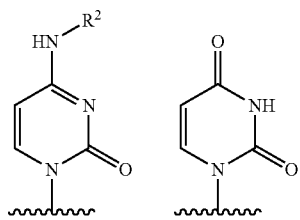

(wherein $R^2$ represents a hydrogen atom, an acetyl group, an isobutyryl group, or a benzoyl group)

$G^1$ can be used without particular limitations as long as it may function as a protecting group, and publicly known protecting groups used for an amidite compound can be used widely.

Examples of $G^1$ include preferably the following groups.

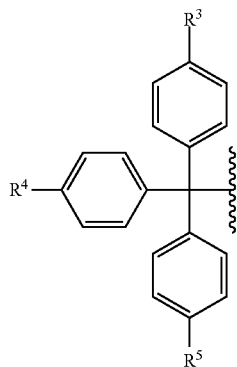

(wherein $R^3$, $R^4$ and $R^5$ are identical to or different from each other, and represent a hydrogen atom or an alkoxy group).

One of $R^3$, $R^4$ and $R^5$ represents a hydrogen atom, and two of the remaining groups thereof represent preferably alkoxy group, and examples of the alkoxy group include particularly preferably a methoxy group.

$G^2$ can be used without particular limitations as long as it may function as a protecting group, and publicly known protecting groups used for amidite compound can be used widely. Examples of $G^2$ include a hydrogen atom, an alkyl group, an alkenyl group, an alkynyl group, a cycloalkyl group, and any hydrocarbon groups other than the above-mentioned alkyl groups; a haloalkyl group, an aryl group, a heteroaryl group, an arylalkyl group, a cycloalkenyl group, a cycloalkylalkyl group, a cyclylalkyl group, a hydroxyalkyl group, an aminoalkyl group, an alkoxyalkyl group, a heterocyclylalkenyl group, a heterocyclylalkyl group, a heteroarylalkyl group, a silyl group, a silyloxyalkyl group, a mono-, di- or tri-alkylsilyl group, a mono-, di- or tri-alkyl silyloxyalkyl group, and the others, and these groups may be optionally substituted with one or more electron-withdrawing groups.

$G^2$ includes preferably an alkyl group substituted with an electron-withdrawing group. Examples of the electron-withdrawing groups include cyano group, nitro group, alkylsulfonyl group, halogen atom, arylsulfonyl group, trihalomethyl group, trialkylamino group and the others, and preferably cyano group.

$G^2$ includes particularly preferably the below-mentioned groups.

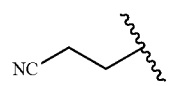 [SMILES: *CCC#N]

$G^3$ are identical to or different from each other, and represent an alkyl group, and two $G^3$ may be combined each other to form a cyclic structure. Preferably, both of $G^3$ represent an isopropyl group.

An alkyl group may be a straight or branched group, and includes preferably an alkyl group having 1 to 12 carbon atoms, more preferably an alkyl group having 1 to 6 carbon atoms. Examples of the alkyl group include methyl group, ethyl group, n-propyl group, isopropyl group, n-butyl group, isobutyl group, tert-butyl group, n-pentyl group, isopentyl group, and hexyl group. The alkyl group used herein encompasses an alkyl moiety such as alkoxy group.

An acyl group represents a straight or branched aliphatic acyl group, or an aromatic acyl group, wherein the total number of carbon atoms including a carbon atom of a carbonyl group is two to twelve of carbon atoms, preferably two to seven of carbon atoms. Examples of the acyl group include an aliphatic acyl group (such as acetyl group, propionyl group, butanoyl group (butyryl group), isobutanoyl group (isobutyryl group), pentanoyl group, hexanoyl group, heptanoyl group, octanoyl group, nonanoyl group, decanoyl group, undecanoyl group and the others); and an aromatic acyl group (such as benzoyl group, 1-naphthoyl group, and 2-naphthoyl group), and preferably include acetyl group, isobutyryl group, or benzoyl group.

Also, examples of the amidite compound of the present invention include any free forms or salt forms of the same compound. Examples of the salts of the amidite compound of the present invention isn't particularly limited, and may be base addition salts, and include salts of addition with inorganic bases (such as sodium salt, magnesium salt, potassium salt, calcium salt, aluminium salt); salts of addition with organic bases (such as methylamine salt, ethylamine salt, and ethanolamine salt); salts of addition with basic amino acids (such as lysine salt, ornithine salt, arginine salt); and salts of addition with base (such as ammonium salt). Also the salts may be acid addition salts, and include salts of addition with mineral acids (such as hydrochloric acid, hydrobromic acid, hydroiodic acid, sulfuric acid, nitric acid, phosphoric acid; organic acids (such as formic acid, acetic acid, propionic acid, oxalic acid, malonic acid, maleic acid, tartaric acid, succinic acid, lactic acid, maleic acid, citric acid, methanesulfonic acid, trifluoromethanesulfonic acid, and ethane sulfonic acid); and salts of addition with acidic amino acids (such as aspartic acid, and glutamic acid).

Step A:

In the present reaction, a glycoside compound represented by general formula (1) is reacted (that is, coupling reaction) with an ether compound represented by formula (2) in the presence of an oxidizing agent and an acid to obtain a glycoside compound represented by general formula (3), which is particularly characterized by adding an oxidizing agent into a reaction system, followed by adding an acid thereto.

Examples of an oxidizing agent include N-halogenated succinimides (such as N-chlorosuccinimide, N-bromosuccinimide, and N-iodosuccinimide and the others); and N-halogenated hydantoins (such as 1,3-diiodo-5,5-dimethyl-hydantoin and the others). In the present invention, N-halogenated succinimide is preferably used, and N-iodosuccinimide is more preferably used.

Examples of the acids include perfluoroalkylcarboxylic acid and salts thereof, alkylsulfonic acid and salts thereof, arylsulfonic acid and salts thereof, perfluoroalkylsulfonic acid and salts thereof, as well as any combinations of two kinds or more thereof. Examples of the bases include metal salts (such as copper salt and silver salt). Examples of the acids include methansulfonic acid, para-toluenesulfonic acid, camphor sulfonic acid, trifluoromethanesulfonic acid, and silver trifluoromethanesulfonate, as well as any combinations of two kinds or more thereof. In the present invention, a trifluoromethanesulfonic acid is preferably used.

Examples of solvents used in the present reaction aren't particularly limited, and include ethers (such as diethyl ether, tetrahydrofuran (THF), cyclopentylmethylether, 2-methyltetrahydrofuran, dimethoxyethane, dioxane and the others); hydrocarbons (such as toluene); nitriles (such as acetonitrile); and halogenated hydrocarbons (such as chlorobenzene and dichloromethane).

The amount of the ether compound represented by formula (2) is within a range of usually 1 to 5 mole(s), preferably 1 to 3 mole(s), and more preferably 1 to 1.5 mole(s), relative to 1 mole of the glycoside compound represented by general formula (1). The amount of the oxidizing agent is within a range of usually 1 to 3 mole(s), preferably 1 to 2 mole(s), and more preferably 1 to 1.5 mole(s), relative to 1 mole of the glycoside compound represented by formula (1). The amount of the acids is within a range of usually 0.1 to 5 mole(s), preferably 0.5 to 3 mole(s), and more preferably 0.5 to 1.5 mole(s), relative to 1 mole of the ether compound represented by formula (1).

The reaction temperature of the present reaction is usually within a range of −80 to 0° C., preferably −60 to −10° C., and more preferably −50 to −40° C. The reaction period of the present reaction is within a range of usually to 12 hour(s), preferably 1 to 8 hour(s), and more preferably 1 to 4 hour(s).

The glycoside compound represented by general formula (1) can be prepared according to a publicly known method, or can be obtained as a commercially available product. The ether compound represented by formula (2) can be prepared according to a publicly known method (see the above-mentioned patent references 1, 2 and 3).

The reaction in step A can be typically conducted by adding an oxidizing agent to a mixture of the glycoside compound represented by general formula (1) and the ether compound represented by formula (2), followed by adding an acid to the resulting mixture. For example, the reaction can be conducted by adding dropwise the glycoside compound represented by general formula (1), the ether compound represented by formula (2), N-iodosuccinimide, and a trifluoromethanesulfonic acid in this order.

Step B:

In the present reaction, hydroxy groups at 3' position and 5' position of the glycoside compound represented by general formula (3) which is obtained in the step A can be deprotected to obtain a glycoside compound represented by general formula (4).

In the deprotection reaction, the protecting agent used can be changed appropriately depending on the protecting groups, and for example, and the deprotecting reaction can be conducted by using a publicly known deprotecting agent. Examples of the deprotecting agent isn't particularly limited, and include, for example, hydrogen fluoride pyridine, triethylamine trihydrofluoride, pyridine hydrofluonate, ammonium fluoride, hydrofluoric acid, and tetrabutylammonium fluoride.

The amount of the deprotecting agent is within a range of usually 0.1 to 20 mole(s), preferably 0.2 to 10 mole(s), and more preferably 1 to 5 mole(s), relative to 1 mole of the glycoside compound represented by general formula (3).

Examples of solvents used in the present reaction aren't particularly limited, and include ketones (such as acetone); ethers (such as diethyl ether, tetrahydrofuran (THF)), hydrocarbons (such as toluene), alcohols (such as methanol, and ethanol), and nitriles (such as acetonitrile).

The reaction temperature of the present reaction is within a range of usually 0 to 100° C., preferably 10 to 60° C., and more preferably 10 to 30° C. The reaction period of the present reaction is within a range of usually 30 minutes to 72 hour(s), and preferably 2 to 24 hour(s).

Step C:

In the present reaction, a protecting group $G^1$ can be introduced into a hydroxy group at 5' position of the glycoside compound represented by general formula (4) which is obtained in the step (B), followed by subjecting the hydroxy group at 3' position to a phosphoramidation reaction to obtain an amidite compound represented by general formula (I).

In the present reaction, an introduction of the protecting group $G^1$ and a phosphoramidation reaction can be conducted at the same time (that is, one step), or a phosphoramidation reaction can be conducted after introducing the protecting group $G^1$, or the protecting group $G^1$ can be introduced after the phosphoramidation reaction is conducted. Particularly preferably, the phosphoramidation reaction is conducted after the protecting group $G^1$ is introduced.

In the introduction reaction of the protecting group $G^1$, the reagent for introducing the protecting group can be selected appropriately depending on $G^1$, and include, for example, 4,4'-dimethoxytritylchloride and the others. The solvents aren't particularly limited, and include, for example, aromatic solvents (such as toluene and pyridine), nitriles (such as acetonitrile), and ethers (such as tetrahydrofuran). The reaction temperature of the reaction is usually within a range of 0 to 100° C., preferably 10 to 60° C., and more preferably 20 to 30° C. The reaction period of the present reaction is within a range of usually 30 minutes to 24 hour(s), and preferably 1 to 8 hour(s). The amount of the reagent for introducing a protecting group is within a range of usually 1 to 100 mole(s), preferably 1 to 20 mole(s), and more preferably 1 to 5 mole(s), relative to 1 mole of the glycoside compound represented by general formula (4).

In the phosphoramidation reaction, the reagent for phosphoramidation can be selected appropriately depending on $G^2$ and $G^3$, and include, for example, 2-cyanoethyl-N,N,N',N'-tetraisopropyldiamidite and the others. The solvents aren't particularly limited, and include, for example, nitriles (such as acetonitrile), ethers (such as tetrahydrofuran), and halogenated hydrocarbons (such as dichloromethane). The reaction temperature of the reaction is usually within a range of 0 to 40° C., and preferably 20 to 40° C. The reaction period of the present reaction is within a range of usually 30 minutes to 24 hour(s), and preferably 1 to 6 hour(s). The amount of the reagent for introducing a protecting group is within a range of usually to 20 mole(s), preferably 1 to 5 mole(s), and more preferably 1 to 1.5 mole(s), relative to 1 mole of the glycoside compound represented by general formula (4).

The reaction products obtained in any steps of step A to Step C can be worked up (such as purification, washing, and concentration and the others) according to a publicly known method.

In the step of preparing the glycoside compound represented by general formula (3) according to the process of the present invention, the formation of impurity materials having the same molecular weight can be suppressed. As a result, the amidite compound represented by general formula (I) as a desired compound can be prepared in a high purity.

EXAMPLES

Hereinafter, the present invention is explained in more detail by working examples, and the present invention isn't limited to these examples.

Example 1

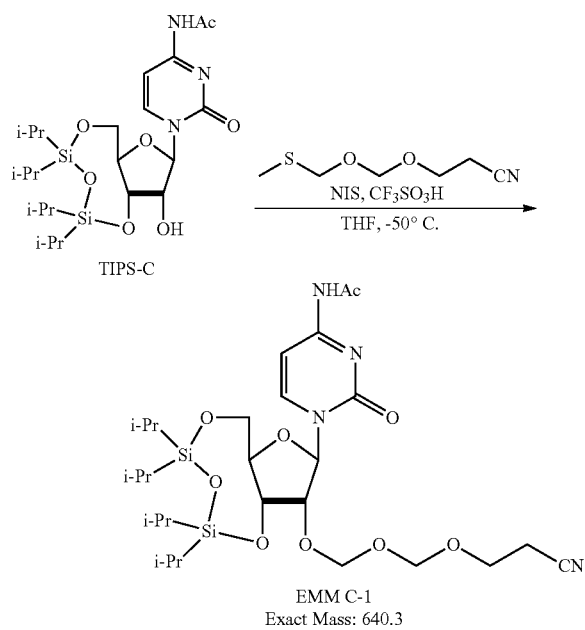

N⁴-Acetyl-3',5'-O-(tetraisopropyldisiloxan-1,3-diyl)cytidine (TIPS-C) (10.0 g, 19.0 mmol), and toluene (50 mL) were added to a flask, and the solution was concentrated to 30 mL. After tetrahydrofuran (22 mL) was added thereto, the reaction solution was cooled to −50° C., and thereto were added dropwise 2-cyanoethoxymethyl methylthiomethyl ether (hereinafter, referred to as "EMM reagent") (4.58 g, 28.4 mmol), a solution of N-iodosuccinimide (5.76 g, 25.6 mmol) in tetrahydrofuran (13 mL), and trifluoromethanesulfonic acid (4.27 g, 28.5 mmol) in this order. After the reaction mixture was stirred at −50° ° C. for 2 hours, the reaction solution was added to an ice-cooled aqueous solution consisting of sodium hydrogen carbonate (3.5 g), sodium thiosulfate pentahydrate (10.0 g) and water (65 mL), and the mixture solution was separated by a separatory funnel at room temperature. The organic layer was further washed with a solution consisting of sodium hydrogen carbonate (1.75 g), sodium thiosulfate pentahydrate (5.0 g) and water (32.5 mL). The organic layer was concentrated to obtain a crude product containing a desired compound.

When LC-MS analysis was conducted and a scan measurement was conducted in a negative mode at 639.3 of m/z of a desired compound, the peak of a critical impurity material having the same m/z as those of the desired compound showed 0.9% relative to 99.1% of the peak of the desired compound.

Example 2

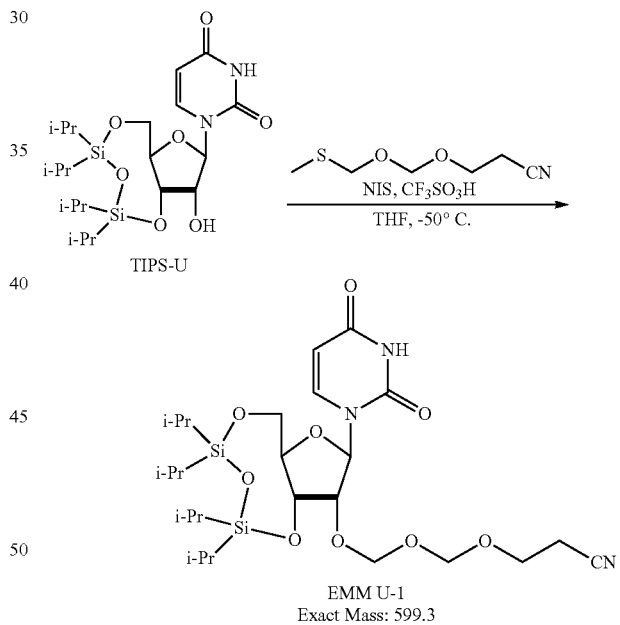

3',5'-O-(Tetraisopropyldisiloxan-1,3-diyl)uridine (TIPS-U) (5.0 g, 10.0 mmol), and toluene (25 mL) were added to a flask, and the reaction mixture was concentrated to 15 mL. After tetrahydrofuran (3.5 mL) was added thereto, the reaction solution was cooled to −50° C., and thereto were added dropwise the EMM reagent (2.48 g, 15.4 mmol), a solution of N-iodosuccinimide (3.18 g, 14.1 mmol) in tetrahydrofuran (6.5 mL), and trifluoromethanesulfonic acid (2.31 g, 15.4 mmol) in this order. After the mixture was stirred at −50° C. for 2 hours, the reaction solution was added to an ice-cooled aqueous solution consisting of sodium hydrogen carbonate (1.75 g), sodium thiosulfate pentahydrate (5.0 g) and water (32.5 mL), and the mixture solution was separated by a separatory funnel at room temperature. The organic layer was further washed with a solution consisting of sodium hydrogen carbonate (0.85 g), sodium thiosulfate pentahydrate (2.5 g) and water (16 mL). The organic layer was concentrated to obtain a crude product containing a desired compound.

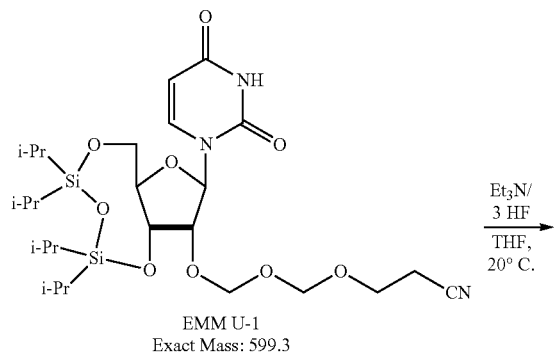

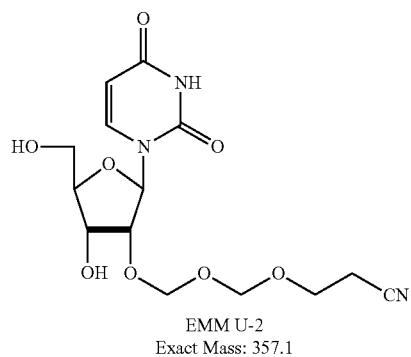

The above-mentioned crude EMM U-1 was solubilized in tetrahydrofuran (15 mL) and acetone (15 mL), and thereto was added hydrogen trifluoride/triethylamine (1.82 g, 11.3 mmol), and the mixture was stirred at 20° C. for 17 hours. The reaction solution was poured to tert-butyl methyl ether (50 mL), and the mixture was stirred for 1 hour. The reaction solution was filtered, and the resulting solids were washed with tert-butyl methyl ether (10 mL), and the solids were dried under reduced pressure to obtain a desired compound (3.01 g, yield 84%).

When LC-MS analysis was conducted and a scan measurement was conducted in a negative mode at 392.1 of m/z of a desired compound (adducts with chloride ions derived from an equipment or glassware and so on), the peak of a critical impurity material having the same m/z as those of the desired compound showed 0.4% relative to 99.6% of the peak of the desired compound.

Example 3

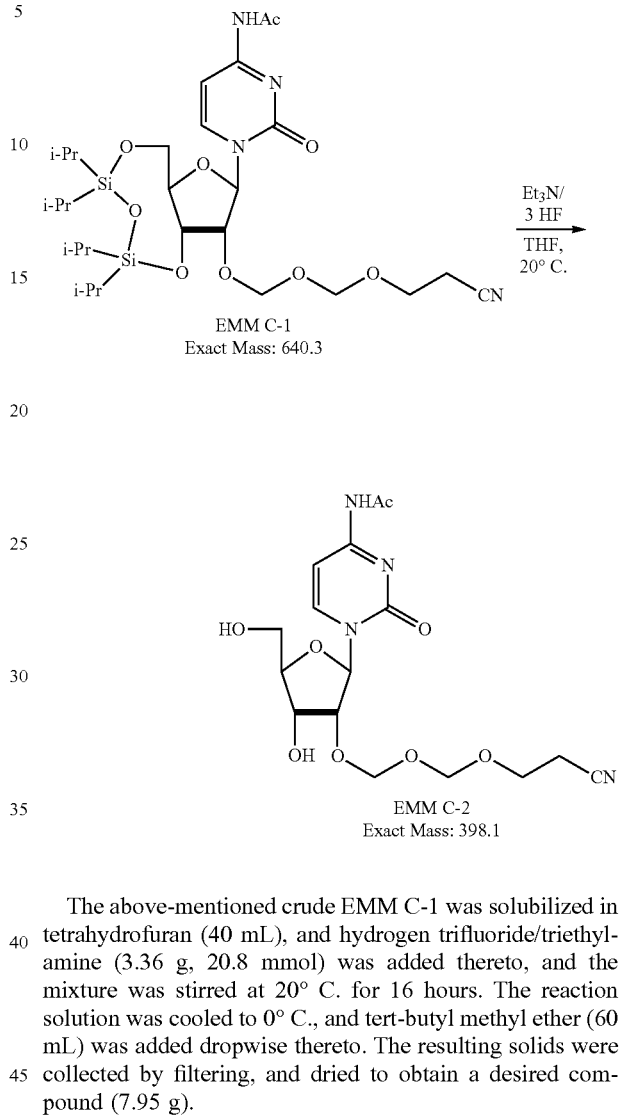

The above-mentioned crude EMM C-1 was solubilized in tetrahydrofuran (40 mL), and hydrogen trifluoride/triethylamine (3.36 g, 20.8 mmol) was added thereto, and the mixture was stirred at 20° C. for 16 hours. The reaction solution was cooled to 0° C., and tert-butyl methyl ether (60 mL) was added dropwise thereto. The resulting solids were collected by filtering, and dried to obtain a desired compound (7.95 g).

Example 4

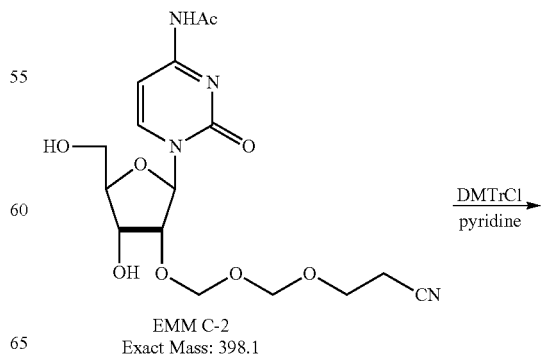

15

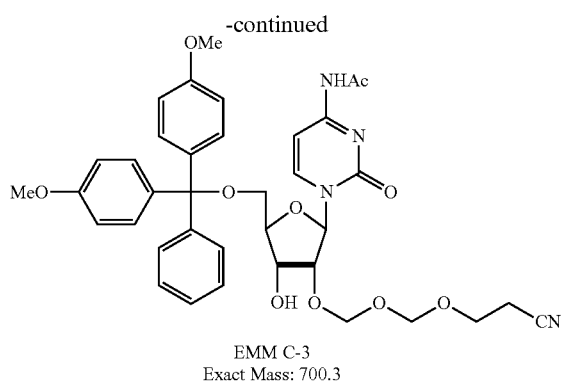

EMM C-3
Exact Mass: 700.3

The above-mentioned crude EMM C-2 (7.0 g, 17.6 mmol) was solubilized in pyridine (35 mL), acetonitrile (14 mL) and toluene (35 mL), and the mixture was cooled to 0° C. 4,4'-Dimethoxy tritylchloride (7.14 g, 21.1 mmol) was added thereto, and the mixture was stirred at 20° C. for 4 hours. Methanol (3.5 mL) was added thereto, and the mixture was stirred for 5 minutes, and the reaction solution was poured into a solution of sodium hydrogen carbonate (1.75 g) and water (35 mL) while washing with toluene (7 mL), and the mixture was separated by a separatory funnel at room temperature. Next, the organic layer was washed with a solution consisting of sodium hydrogen carbonate (1.75 g) and water (35 mL). The organic layer was further washed with a solution consisting of sodium chloride (3.5 g) and water (35 mL), and the organic layer was concentrated into 21 mL. The procedure in which the mixture was concentrated to 21 mL while adding toluene (28 ml) was repeated three times to obtain a crude product containing a desired compound. The resulting mixture was purified by a silica gel column chromatography (heptane/ethyl acetate-acetone 1:1 solution=40/60 to 10/90) to obtain a desired compound (6.42 g, 61% yield from TIPS-C).

Example 5

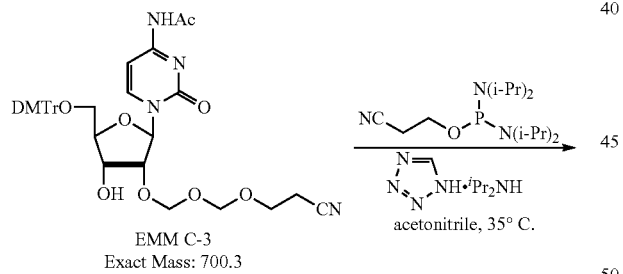

16

To the above-mentioned EMM C-3 (6.0 g, 8.6 mmol) was added acetonitrile (18 mL), and thereto were added diisopropylamine tetrazolide (1.68 g, 9.8 mmol), and 2-cyanoethyl N,N,N',N'-tetraisopropyl phosphordiamidite (3.09 g, 10.3 mmol) at 25° C., and the mixture was stirred at 35° C. for 2 hours. The reaction solution was poured to a solution consisting of toluene (60 mL), water (30 mL) and sodium hydrogen carbonate (1.5 g), and the mixture was separated by a separatory funnel at room temperature. The organic layer was washed with a solution consisting of DMF (30 mL) and water (30 mL) four times, and water (30 mL) twice, and a solution consisting of sodium chloride (3.0 g) and water (30 mL) once, respectively. To the organic layer was added sodium sulfate (3.0 g), and the mixture was filtered, and concentrated to 18 mL to obtain a crude product containing a desired compound. The mixture was purified by a silica gel column chromatography (heptane/acetone=60/40 to 30/70) to obtain a desired compound (6.45 g, 84% yield from EMM C-3).

Example 6

TIPS-C

NIS, CF$_3$SO$_3$H
THF, -50° C.

CEM C-1
Exact Mass: 610.3

$N^4$-Acetyl-3',5'-O-(tetraisopropyldisiloxan-1,3-diyl)cytidine (TIPS-C) (1.0 g, 1.9 mmol) was solubilized in tetrahydrofuran (10 mL), and thereto were added methylthiomethyl 2-cyanoethyl ether (hereinafter, referred to "CEM reagent") (0.37 g, 2.8 mmol) and molecular sieve 4A (0.8 g), and the mixture was stirred at −45° C. under nitrogen atmosphere for 30 minutes. N-Iodosuccinimide (0.64 g, 2.8 mmol) was added thereto, followed by adding dropwise trifluoromethanesulfonic acid (0.42 g, 2.8 mmol) thereto, and the mixture was stirred at −45° C. for 30 minutes. To the reaction solution was added triethylamine (1.6 mL), and the mixture was filtered, and thereto was then added ethyl acetate, and the organic layer was washed with a mixture of water (10 mL), sodium thiosulfate pentahydrate (1.0 g) and sodium hydrogen carbonate (0.35 g) twice. The solvent was evaporated to obtain a crude product containing a desired compound.

When LC-MS analysis was conducted and a scan measurement was conducted in a negative mode at 609.3 of m/z of a desired compound, the peak of a critical impurity material having the same m/z as those of the desired compound showed 0.07% relative to 99.93% of the peak of the desired compound.

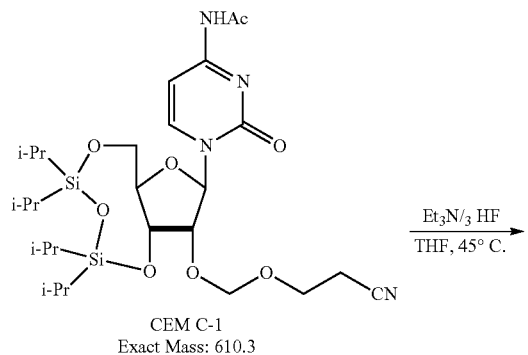

CEM C-1
Exact Mass: 610.3

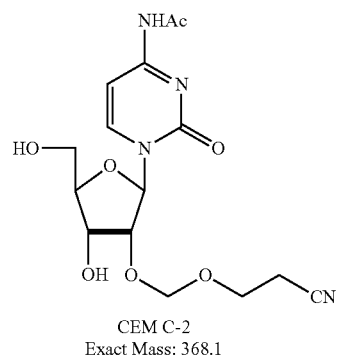

CEM C-2
Exact Mass: 368.1

The above-mentioned crude CMM C-1 was solubilized in tetrahydrofuran (6 mL), and thereto was added hydrogen trifluoride/triethylamine (0.37 g, 2.2 mmol) at 25° C., and the mixture was stirred at 45° C. for 2 hours. The resulting participates were recovered by a suction filtration, washed with tetrahydrofuran, and dried to obtain a desired compound (0.68 g, Yield 97%).

Example 7

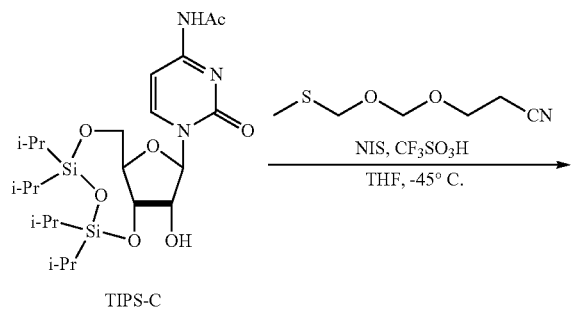

TIPS-C

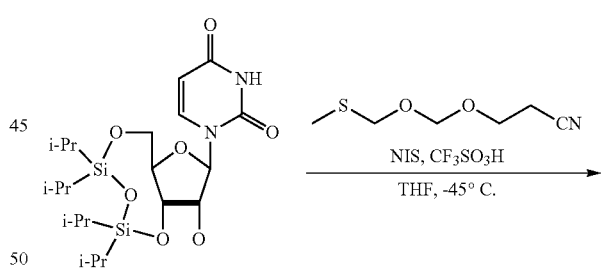

EMM C-1
Exact Mass: 640.3

$N^4$-Acetyl-3',5'-O-(tetraisopropyldisiloxan-1,3-diyl)cytidine (TIPS-C) (3.0 g, 5.7 mmol) was co-distilled with toluene (15 mL) three times, and the solvents were evaporated with a vacuum pump. Under nitrogen atmosphere, the residue was solubilized in tetrahydrofuran (30 mL), and the solution was cooled to −45° C. To this solution were added dropwise the EMM reagent (2.8 g, 18 mmol), N-iodosuccinimide (2.0 g, 9.0 mmol), and trifluoromethanesulfonic acid (1.3 g, 8.8 mmol) in this order. After the mixture was stirred at −45° C. for 5 hours, triethylamine was added to the reaction solution to quench. The reaction solution was added to an ice-cooled solution consisting of ethyl acetate (30 mL), sodium hydrogen carbonate (1.5 g), sodium thiosulfate pentahydrate (3.0 g), and water (30 mL), and the mixture was separated by a separatory funnel at room temperature. The organic layer was concentrated to obtain a crude product containing a desired compound.

When LC-MS analysis was conducted and a scan measurement was conducted in a negative mode at 639.3 of m/z of a desired compound, the peak of a critical impurity material having the same m/z as those of the desired compound showed 0.13% relative to 99.87% of the peak of the desired compound.

Example 8

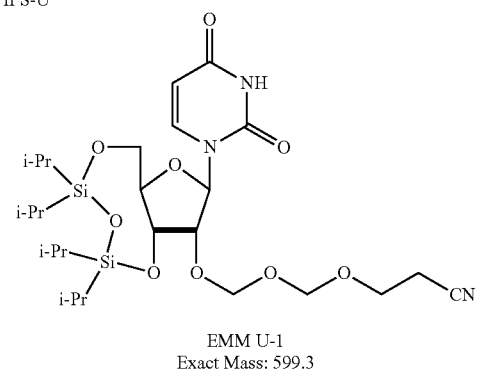

TIPS-U

EMM U-1
Exact Mass: 599.3

3',5'-O-(Tetraisopropyldisiloxan-1,3-diyl)uridine (TIPS-U) (3.0 g, 6.0 mmol) was solubilized in tetrahydrofuran (30 mL) under nitrogen atmosphere, and the solution was cooled to −45° C. To the solution were added dropwise the EMM reagent (1.56 g, 9.7 mmol), N-trifluoromethanesulfonic acid (1.44 g, 9.7 mmol) in this order. After the mixture was stirred at −45° C. for 5 hours, triethylamine was added to the reaction solution to quench. The reaction solution was added to an ice-cooled aqueous solution consisting of sodium hydrogen carbonate (1.5 g), sodium thiosulfate pentahydrate (3.0 g), water (30 ml) and ethyl acetate (15 mL), and the mixture was separated by a separatory funnel at room temperature. The organic layer was further washed with a solution consisting of sodium hydrogen carbonate (1.5 g), sodium thiosulfate pentahydrate (3.0 g) and water (30 mL). The organic layer was concentrated to obtain a crude product containing a desired compound. The resulting crude product was purified by a silica gel column chromatography (ethyl acetate:heptane=1:1) to obtain a desired compound (3.0 g, Yield 83%).

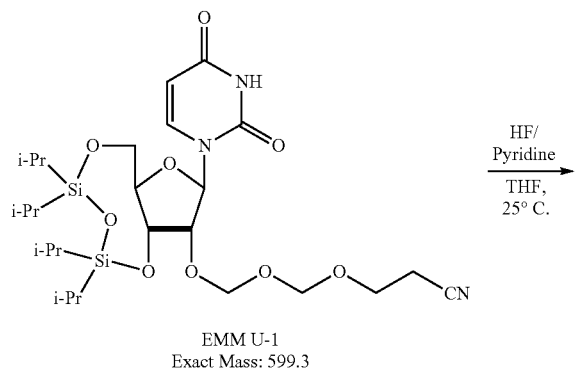

EMM U-1
Exact Mass: 599.3

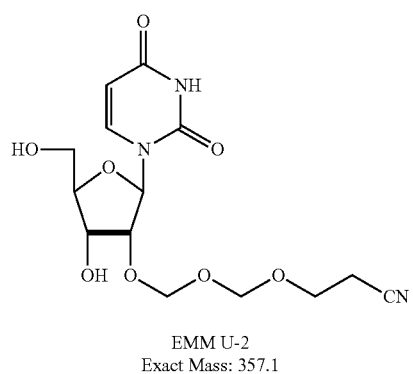

EMM U-2
Exact Mass: 357.1

The above-mentioned EMM U-1 (2.0 g, 3.3 mmol) was solubilized in tetrahydrofuran (8 mL), and thereto was added hydrogen fluoride pyridine (65.5%, 0.81 g), and the mixture was stirred at 25° C. for 17 hours. The resulting participates were collected by filtering to obtain a desired compound (1.10 g, Yield 92%).

When LC-MS analysis was conducted and a scan measurement was conducted in a negative mode at 356.1 of m/z of a desired compound, the peak of a critical impurity material having the same m/z as those of the desired compound didn't detected.

Comparative Experiment 1

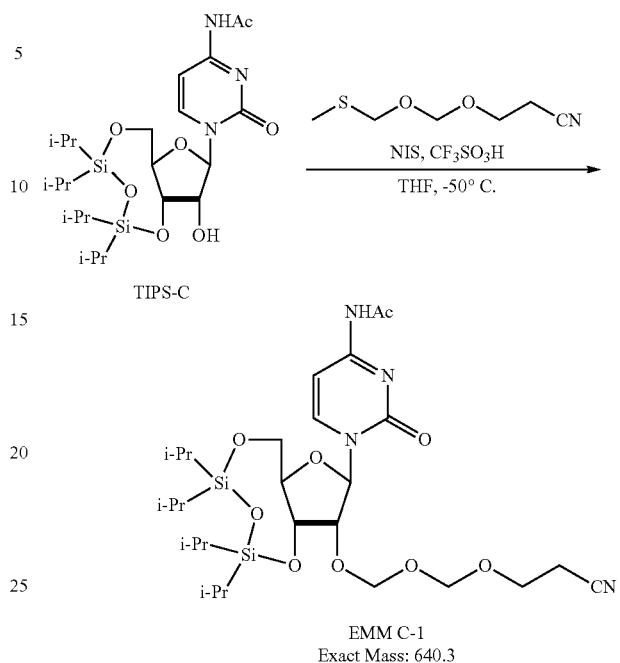

EMM C-1
Exact Mass: 640.3

$N^4$-Acetyl-3',5'-O-(tetraisopropyldisiloxan-1,3-diyl)cytidine (TIPS-C) (10.0 g, 19.0 mmol) and toluene (50 mL) were added to a flask, and the solution was concentrated to 30 mL. Thereto was added tetrahydrofuran (22 mL), and the solution was cooled to −50° C., and thereto were then added dropwise the EMM reagent (4.58 g, 28.4 mmol), trifluoromethanesulfonic acid (4.27 g, 28.5 mmol), and a solution of N-iodosuccinimide (5.76 g, 25.6 mmol) in tetrahydrofuran (13 mL) in this order. After the mixture was stirred at −50° C. for 1 hour, the reaction solution was added to an ice-cooled aqueous solution consisting of sodium hydrogen carbonate (3.5 g), sodium thiosulfate pentahydrate (10.0 g) and water (65 mL), and the mixture was separated by a separatory funnel at room temperature. The organic layer was further washed with a solution consisting of sodium hydrogen carbonate (1.75 g), sodium thiosulfate pentahydrate (5.0 g) and water (32.5 mL). The organic layer was concentrated to obtain a crude product containing a desired compound.

When LC-MS analysis was conducted and a scan measurement was conducted in a negative mode at 639.3 of m/z of a desired compound, the peak of a critical impurity material having the same m/z as those of the desired compound showed 3.6% relative to 96.4% of the peak of the desired compound.

Comparative Experiment 2

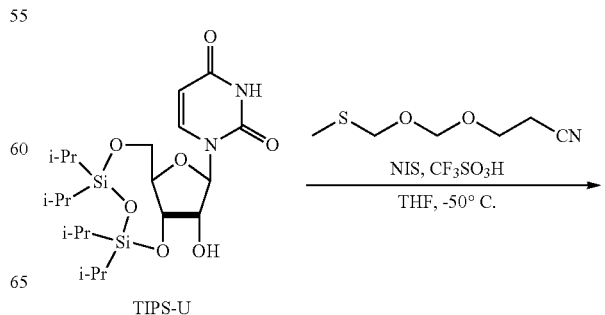

TIPS-U

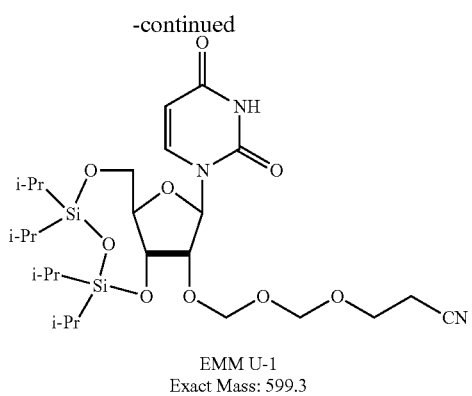

EMM U-1
Exact Mass: 599.3

3′,5′-O-(Tetraisopropyldisiloxan-1,3-diyl)uridine (TIPS-U) (5.0 g, 10.0 mmol), and toluene (25 mL) were added to a flask, and the solution was concentrated to 15 mL. After tetrahydrofuran (3.5 mL) was added thereto, the solution was cooled to −50° C., and thereto were added dropwise the EMM reagent (2.48 g, 15.4 mmol), trifluoromethanesulfonic acid (2.31 g, 15.4 mmol), and a solution of N-iodosuccinimide (3.18 g, 14.1 mmol) in tetrahydrofuran (6.5 mL) in this order. After the mixture was stirred at −50° C. for 2 hours, the reaction solution was added to an ice-cooled aqueous solution consisting of sodium hydrogen carbonate (1.75 g), sodium thiosulfate pentahydrate (5.0 g), and water (32.5 mL), and the mixture was separated by a separatory funnel at room temperature. The organic layer was further washed with a solution consisting of sodium hydrogen carbonate (0.85 g), sodium thiosulfate pentahydrate (2.5 g), and water (16 mL). The organic layer was concentrated to obtain a crude product containing a desired compound.

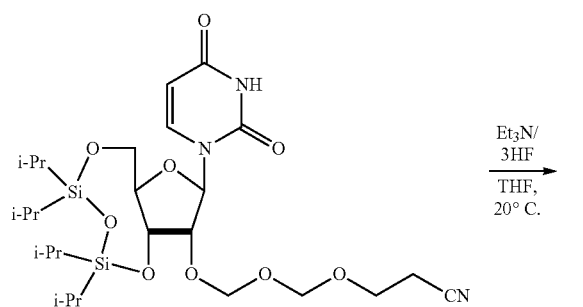

EMM U-1
Exact Mass: 599.3

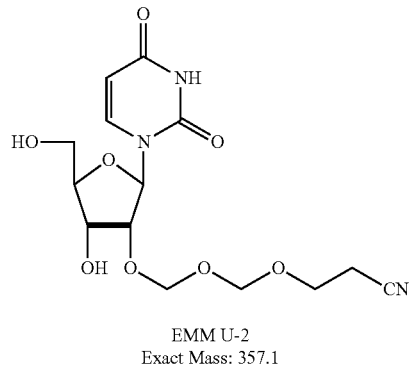

EMM U-2
Exact Mass: 357.1

The above-mentioned EMM U-1 was solubilized in tetrahydrofuran (15 mL) and acetone (15 mL), and thereto were added hydrogen trifluoride/triethylamine (1.82 g, 11.3 mmol), and the reaction solution was stirred at 20° C. for 17 hours. The reaction solution was poured to tert-butyl methyl ether (50 mL), and the mixture was stirred for hour. The reaction was filtered, and the resulting solids were washed with tert-butyl methyl ether (10 mL), and the solids were dried under reduced pressure to obtain a desired compound (3.05 g, Yield 85%).

When LC-MS analysis was conducted and a scan measurement was conducted in a negative mode at 392.1 of m/z of a desired compound (adducts with chloride ions derived from an equipment or glassware and so on), the peak of a critical impurity material having the same m/z as those of the desired compound showed 7.4% relative to 92.6% of the peak of the desired compound.

Comparative Experiment 3

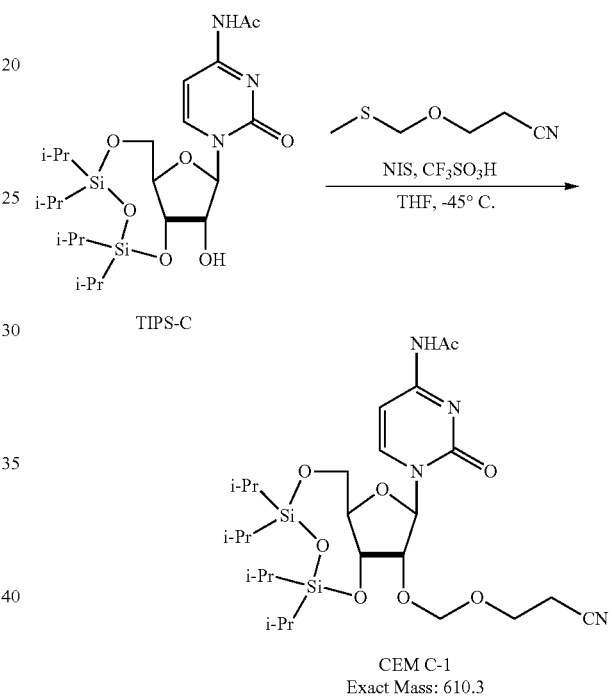

CEM C-1
Exact Mass: 610.3

$N^4$-Acetyl-3′,5′-O-(tetraisopropyldisiloxan-1,3-diyl)cytidine (TIPS-C) (1.0 g, 1.9 mmol) was solubilized in tetrahydrofuran (10 mL), and thereto were added the CEM reagent (0.37 g, 2.8 mmol) and molecular sieve 4A (0.8 g), and the mixture was stirred at −45° ° C. under nitrogen atmosphere for 30 minutes. Thereto was added dropwise trifluoromethanesulfonic acid (0.42 g, 2.8 mmol), followed by adding N-iodosuccinimide (0.64 g, 2.8 mmol), and the mixture was stirred at −45° C. for 30 minutes. To the reaction solution was added triethylamine (1.6 mL), and the mixture was filtered, and to the filtrates was added ethyl acetate, and the organic layer was washed with a mixture solution of water (10 mL), sodium thiosulfate pentahydrate (1.0 g), and sodium hydrogen carbonate (0.35 g) twice. The solvent was evaporated to obtain a crude product containing a desired compound.

When LC-MS analysis was conducted and a scan measurement was conducted in a negative mode at 609.3 of m/z of a desired compound, the peak of a critical impurity material having the same m/z as those of the desired compound showed 2.7% relative to 97.3% of the peak of the desired compound.

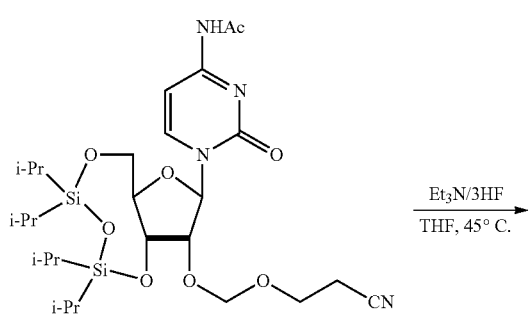

CEM C-1
Exact Mass: 610.3

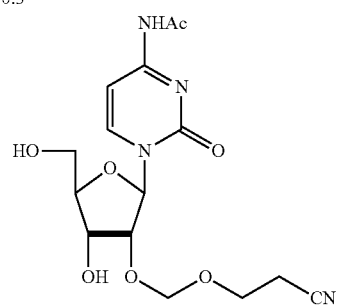

CEM C-2
Exact Mass: 368.1

The above-mentioned CMM C-1 was solubilized in tetrahydrofuran (6 mL), and thereto was added hydrogen trifluoride/triethylamine (0.37 g, 2.2 mmol) at 25° C., and the mixture was stirred at 45° C. for 2 hours. The resulting participates were collected by a suction filtration, washed with tetrahydrofuran, and dried to obtain a desired compound (0.63 g, Yield 90%).

Comparative Experiment 4

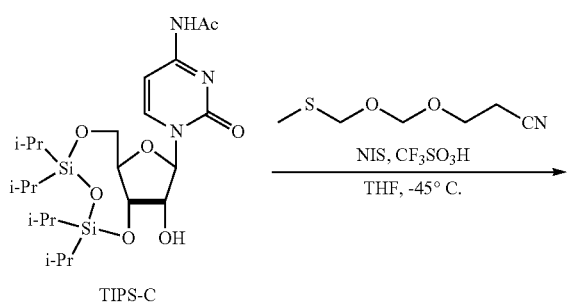

EMM C-1
Exact Mass: 640.3

$N^4$-Acetyl-3',5'-O-(tetraisopropyldisiloxan-1,3-diyl)cytidine (TIPS-C) (3.0 g, 5.7 mmol) was co-distilled with toluene (15 mL) three times, and the solvents were evaporated with a vacuum pump. Under nitrogen atmosphere, the residue was solubilized in tetrahydrofuran (30 mL) under nitrogen atmosphere, and the solution was cooled to −45° C. To this solution were added dropwise the EMM reagent (2.8 g, 18 mmol), trifluoromethanesulfonic acid (1.3 g, 8.8 mmol), and N-iodosuccinimide (2.0 g, 9.0 mmol) in this order. After the mixture was stirred at −45° C. for 5 hours, triethylamine was added thereto to quench. The reaction solution was added to an ice-cooled aqueous solution consisting of ethyl acetate (30 mL), sodium hydrogen carbonate (1.5 g), sodium thiosulfate pentahydrate (3.0 g), and water (30 mL), and the mixture was separated by a separatory funnel at room temperature. The organic layer was concentrated to obtain a crude product containing a desired compound.

When LC-MS analysis was conducted and a scan measurement was conducted in a negative mode at 639.3 of m/z of a desired compound, the peak of a critical impurity material having the same m/z as those of the desired compound showed 2.3% relative to 97.7% of the peak of the desired compound.

Comparative Experiment 5

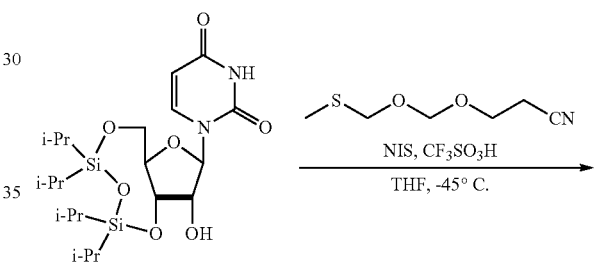

TIPS-U

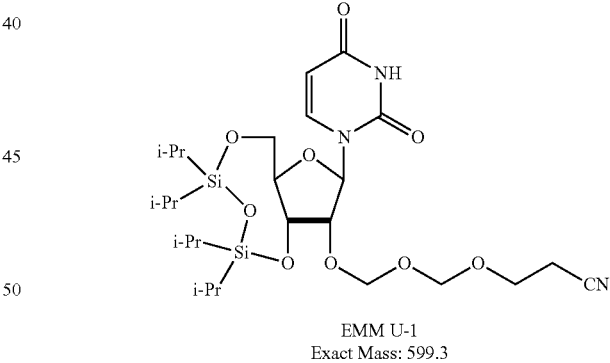

EMM U-1
Exact Mass: 599.3

3',5'-O-(Tetraisopropyldisiloxan-1,3-diyl)uridine (TIPS-U) (3.0 g, 6.0 mmol) was solubilized in tetrahydrofuran (30 mL) under nitrogen atmosphere, and the solution was cooled to −45° C. To this solution were added dropwise the EMM reagent (1.56 g, 9.7 mmol), trifluoromethanesulfonic acid (1.44 g, 9.7 mmol) and N-iodosuccinimide (2.16 g, 9.7 mmol) in this order. After the mixture was stirred at −45° C. for 5 hours, triethylamine was added thereto to quench. The reaction solution was added to an ice-cooled aqueous solution consisting of sodium hydrogen carbonate (1.5 g), sodium thiosulfate pentahydrate (3.0 g), and ethyl acetate (15 mL), and the mixture was separated by a separatory funnel at room temperature. The organic layer was further washed with a solution of sodium hydrogen carbonate (1.5 g), sodium thiosulfate pentahydrate (3.0 g), and water (30 mL). The organic layer was concentrated to obtain a crude product containing a desired compound. The resulting crude product was purified by a silica gel column chromatography (ethyl acetate:heptane=1:1) to obtain a desired compound (2.82 g, Yield 78%).

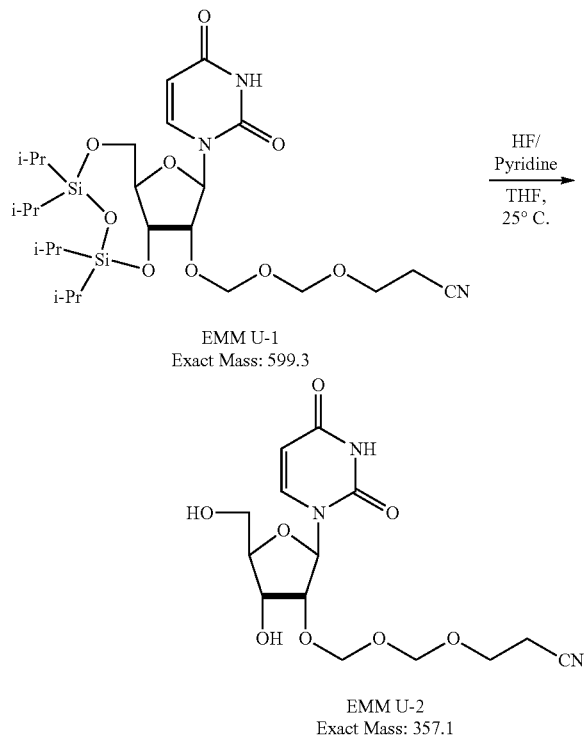

EMM U-1
Exact Mass: 599.3

EMM U-2
Exact Mass: 357.1

The above-mentioned EMM U-1 (2.0 g, 3.3 mmol) was solubilized in THF (8 mL), and thereto was added hydrogen fluoride pyridine (65.5%, 0.81 g), and the mixture was stirred at 25° C. for 17 hours. The resulting participates were collected by filtering to obtain a desired compound (1.08 g, Yield 90%).

When LC-MS analysis was conducted and a scan measurement was conducted in a negative mode at 356.1 of m/z of a desired compound, the peak of a critical impurity material having the same m/z as those of the desired compound showed 1.1% relative to 98.9% of the peak of the desired compound.

TABLE 1

| Desired compound | Critical impurity material having the same m/z as those of desired compound (LC-MS) | |
| --- | --- | --- |
| | Addition Order 1 of Reagents | Addition Order 2 of Reagents |
| EMM C-1 | 0.9% (Example 1) | 3.6% (Comparative Example 1) |
| EMM C-1 | 0.13% (Example 7) | 2.3% (Comparative Example 4) |
| EMM U-2 | 0.4% (Example 2) | 7.4% (Comparative Example 2) |
| EMM U-2 | N.D. (Example 8) | 1.1% (Comparative Example 5) |
| CEM C-1 | 0.07% (Example 6) | 2.7% (Comparative Example 3) |

Addition Order 1 of Reagents:
EMM reagent or CEM reagent, N-iodosuccinimide, and trifluoromethanesulfonic acid in this order,
Addition Order 2 of Reagents:
EMM reagent or CEM reagent, trifluoromethanesulfonic acid, and N-iodosuccinimide in this order As shown in the above Table 1, an addition of N-iodosuccinimide, followed by addition of trifluoromethanesulfonic acid can suppress a production of impurity materials, which can produce a desired compound with higher purity.

The invention claimed is:

1. A process for preparing a glycoside compound represented by formula (3), the process comprising:
reacting a glycoside compound represented by formula (1) with an ether compound represented by formula (2) in the presence of an oxidizing agent and an acid to prepare a glycoside compound represented by formula (3),
wherein the oxidizing agent is added to a mixture of the glycoside compound represented by formula (1) and the ether compound represented by formula (2), followed by adding an acid thereto:

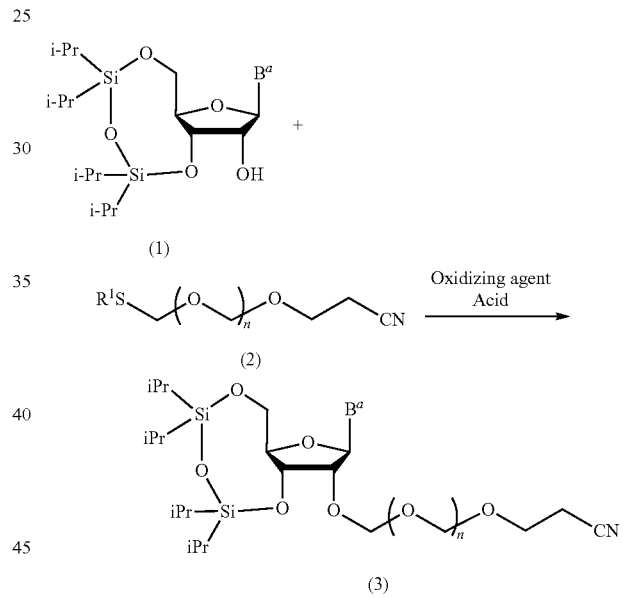

wherein
$B^a$ represents a cytosine group which may be optionally substituted with acyl group, or an uracil group,
$R^1$ represents a C1 to C6 alkyl group or a phenyl group, and
n is 0 or 1,
wherein
the oxidizing agent is selected from the group consisting of N-halogenated succinimide and N-halogenated hydantoin, and
the acid is at least one selected from the group consisting of perfluoroalkylcarboxylic acid and salts thereof, alkylsulfonic acid and salts thereof, arylsulfonic acid and salts thereof, perfluoroalkylsulfonic acid and salts thereof, and combinations thereof.

2. The process according to claim 1, wherein n is 1.

3. The process according to claim 1, wherein n is 0.

4. The process according to claim 1, wherein the oxidizing agent is N-halogenated succinimide.

5. The process according to claim 1, wherein the oxidizing agent is N-iodosuccinimide.

6. The process according to claim 1, wherein the acid is at least one acid selected from the group consisting of trifluoromethanesulfonic acid, silver trifluoromethanesulfonate, and methanesulfonic acid.

7. The process according to claim 1, wherein the acid is trifluoromethanesulfonic acid.

8. The process according to claim 1, wherein tetrahydrofuran is used as a solvent.

9. The process according to claim 1, wherein $R^1$ represents a methyl group.

10. The process according to claim 1, wherein $B^a$ represents a cytosine group substituted with acetyl group, or an unsubstituted uracil group.

11. A process for preparing an amidite compound represented by formula (I):

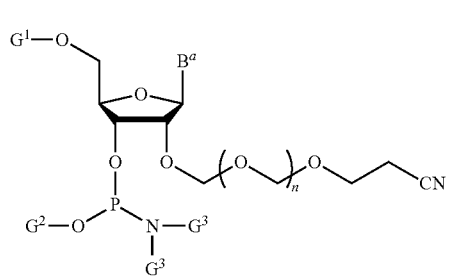

(I)

wherein $B^a$ represents a cytosine group which may be optionally substituted with acyl group, or an uracil group, n is 0 or 1, $G^1$ and $G^2$ are identical to or different from each other, and represent a protecting group for a hydroxy group, and $G^3$ are identical to or different from each other, and represent an alkyl group, the process comprising:

(A) reacting a glycoside compound represented by formula (1) with an ether compound represented by formula (2) according to the process according to claim 1 to prepare a glycoside compound represented by general formula (3):

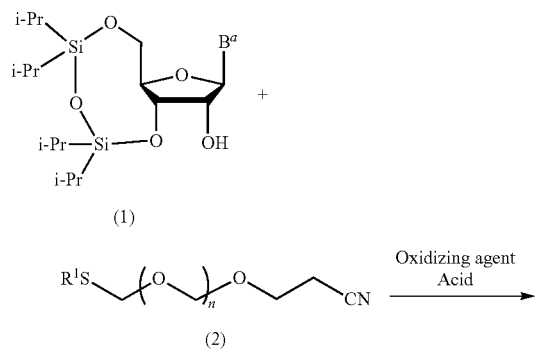

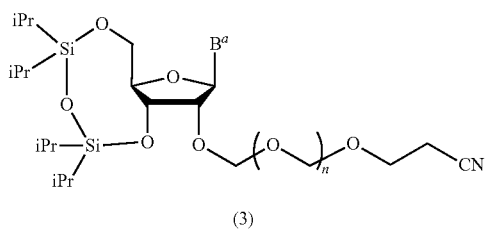

(3)

wherein $B^a$ and n are the same as defined in formula (I), and $R^1$ represents a C1 to C6 alkyl group or a phenyl group.

12. The process according to claim 11, further comprising:

(B) deprotecting hydroxy groups at 3' position and 5' position of the glycoside compound represented by formula (3) to prepare a glycoside compound represented by formula (4):

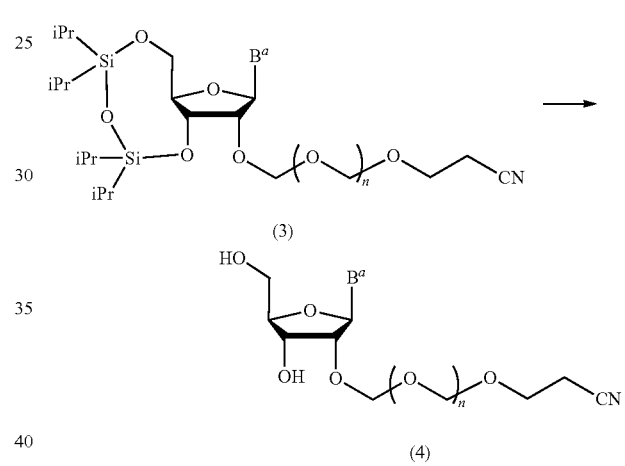

wherein $B^a$ and n are the same as defined in claim 11.

13. The process according to claim 12, wherein triethylamine trihydrofluoride or pyridine hydrofluorate is used as a deprotecting agent.

14. The process according to claim 12, further comprising:

introducing a protecting group $G^1$ to a hydroxy group at 5' position of the glycoside compound represented by formula (4) which is obtained in (B), followed by subjecting a hydroxy group at 3' position to a phosphoramidation reaction to prepare an amidite compound represented by formula (I):

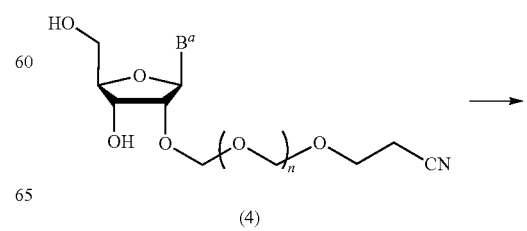

-continued

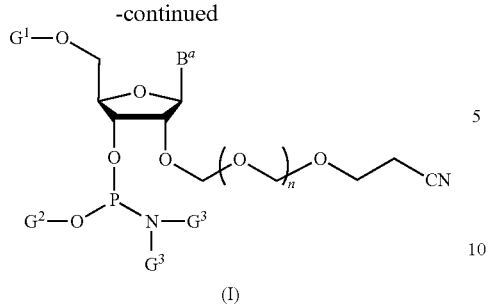

(I)

wherein $B^a$, n, $G^1$, $G^2$ and $G^3$ are the same as defined in claim 12.

15. The process according to claim 14, wherein 4,4'-dimethoxy tritylchloride is used as a reagent for introducing a protecting group for hydroxy group at 5' position.

16. The process according to claim 14, wherein 2-cyanoethyl-N,N,N',N'-tetraisopropylphosphordiamidite as a reagent for phosphoramidation of a hydroxy group at 3' position.

\* \* \* \* \*